(12) United States Patent
Wang et al.

(10) Patent No.: US 7,939,560 B2
(45) Date of Patent: May 10, 2011

(54) FLUORESCENT PARTICLES COMPRISING NANOSCALE ZNO LAYER AND EXHIBITING CELL-SPECIFIC TOXICITY

(75) Inventors: Hua Wang, Boise, ID (US); Denise Wingett, Boise, ID (US); Kevin Feris, Boise, ID (US); Madhusudan R Kongara, Boise, ID (US); Alex Punnoose, Boise, ID (US)

(73) Assignee: Boise State University, Boise, ID (US)

( * ) Notice: Subject to any disclaimer, the term of this patent is extended or adjusted under 35 U.S.C. 154(b) by 284 days.

(21) Appl. No.: 12/235,575

(22) Filed: Sep. 22, 2008

(65) Prior Publication Data

US 2009/0137666 A1    May 28, 2009

Related U.S. Application Data

(60) Provisional application No. 60/974,461, filed on Sep. 22, 2007.

(51) Int. Cl.
*A61K 31/315*   (2006.01)
*A61K 9/28*   (2006.01)

(52) U.S. Cl. ....... 514/494; 427/2.14; 977/701; 977/712; 977/715

(58) Field of Classification Search ................ 514/494; 427/2.14; 977/701, 712, 715
See application file for complete search history.

(56) References Cited

U.S. PATENT DOCUMENTS

| 7,241,399 B2 * | 7/2007 | Haubold et al. ....... 252/301.4 R |
| 2009/0136580 A1 * | 5/2009 | Punnoose et al. ............. 424/489 |
| 2009/0186419 A1 * | 7/2009 | Ying et al. .................... 436/111 |

FOREIGN PATENT DOCUMENTS

| WO | WO 2009/039508 | 3/2009 |
| WO | WO 2009/079056 | 6/2009 |

OTHER PUBLICATIONS

PCT International Search Report, PCT/US2008/077284, Sep. 1, 2009.
Wang, Wingett, Engelard, Feris, Reddy, Turner, Layne, Hanley, Bell, Tenne, Wang, Punnoose, "Fluorescent dye encapsulated ZnO particles with cell-specific toxicity for potential use in biomedical applications", Journal of Material Science: Materials in Medicine (2009) 20:11-22, U.S., published online Jul. 24, 2008.
Hays, Reddy, Graces, Engelhard, Shutthanandan, Luo, Xu, Giles, Wang, Thevuthasa, Punnoose, "Effect of Co doping on the structural, optical and magnetic properties of ZnO nanoparticles", Apr. 27, 2007, Journal of Physics: Condensed Matter (2007) 266203 (24pp), UK, published Jun. 7, 2007.
Reddy, Feris, Wingett, Hanley, Punnoose, "Selective toxicity of zinc oxide nanoparticles to prokaryotic and eukaryotic systems", Applied Physics Letters, May 24, 2007, 90, 213902, U.S.

* cited by examiner

*Primary Examiner* — Raymond J Henley, III
(74) *Attorney, Agent, or Firm* — Pedersen and Company, PLLC; Ken J. Pedersen; Barbara S. Pedersen

(57) ABSTRACT

Multifunctional "smart" nanostructures are disclosed that include fluorescein isothiocyanate (FITC)-encapsulated $SiO_2$ core-shell particles with a nanoscale ZnO finishing layer, wherein an outer ZnO layer is formed on the $SiO_2$-FITC core. These ~200 nm sized particles showed promise toward cell imaging and cellular uptake studies using the bacterium *Escherichia coli* and Jurkat cancer cells, respectively. The FITC encapsulated ZnO particles demonstrated excellent selectivity in preferentially killing Jurkat cancer cells with minimal toxicity to normal primary immune cells (18% and 75% viability remaining, respectively, after exposure to 60 μg/mL) and inhibited the growth of both gram-positive and gram-negative bacteria at concentrations ≧250-500 μg/mL (for *Staphylococcus aureus* and *Escherichia coli*, respectively). These results indicate that the FITC encapsulated multifunctional particles with nanoscale ZnO surface layer can be used as smart nanostructures for particle tracking, cell imaging, antibacterial treatments and cancer therapy.

9 Claims, 8 Drawing Sheets

US 7,939,560 B2

FLUORESCENT PARTICLES COMPRISING NANOSCALE ZNO LAYER AND EXHIBITING CELL-SPECIFIC TOXICITY

This application claims priority of Provisional Application No. 60/974,461, filed Sep. 22, 2007, and entitled "Fluorescent Dye Encapsulated ZnO Particles with Cell-Specific Toxicity for Cancer Treatment and Bio-medical Applications," the entire disclosure of which is hereby incorporated herein by this reference.

This research was supported in part by NSF-Idaho-EPSCoR Program (EPS-0447689), DoE-EPSCoR grant (DE-FG02-04ER46142), NSF-CAREER award (DMR-0449639), NSF-MRI grants (MRI-052131, MRI-0619793 and MRI-0722699), and NIH awards (1R15AI06277-01A1, 1R43 AR052955-01 and P20RR016454).

BACKGROUND OF THE INVENTION

1. Field of the Invention

This invention relates generally to a new composition of matter, a zinc oxide (ZnO) encapsulated fluorescent dye nanoparticle in about the 200 nm range, with the ZnO outer layer being about 10 nm. More specifically, this invention relates to use of the new nanoparticle material as a fluorescence probe, antibacterial agent, or cancer treatment. Also, this invention relates to ways to make the new material.

2. Background Art

The ongoing worldwide nanotechnology revolution is predicted to impact several areas of biomedical research and other science and engineering applications. Nanoparticle-assisted drug delivery, cell imaging and cancer therapy are important biomedical applications of nanotechnology. Development of core-shell nanostructures that combine multiple functions are of great interest for future nano-bio-technology and biomedical applications. For example, core-shell nanostructures containing a chemotherapeutic drug and a fluorescent dye could be used to release the drug at sites of interest while tracking the exact location of its delivery using imaging methods employing the fluorescence of the dye molecules. When organic dye molecules such as fluoroescein isothiocyanate (FITC) are exposed to harsh environments, they often suffer from freely interacting with solvent molecules, which can result in reduced performance of the dye. Encapsulation of the organic fluorescent dye in a core-shell nanostructure can not only add optical functionality, allowing the particles to be tracked and imaged easily, but can also enhance the stability and performance of the dye by protecting it from photobleaching and quenching from the background medium.

Several groups have employed fluorescent core-shell nanoparticles to add functional layers that can destroy disease causing cells, including cancerous cells. Mesoporous fluorescent silica particles developed by adding molecular sieve materials such as MCM-48 were used for site-oriented delivery of chemotherapeutic drugs and cell imaging. Recently, gold coated silica nanoparticles have been used to kill tumor cells via hyperthermia treatments. However, these treatment methods employing either the conventional chemotherapeutic drugs or hyperthermia suffer from lack of significant cell specificity. Both methods can kill normal cells along with cancer cells of interest.

In a recent work (K. M. Reddy, K. Feris, J. Bell, D. G. Wingett, C. Hanley, A. Punnoose, Appl. Phys. Lett. 90, 213902 (2007)), our group demonstrated the ability of identical ~13 nm ZnO nanoparticles to kill bacterial cells at concentrations that are not toxic to human T lymphocytes. *Escherichia coli* (*E. coli*) and *Staphylococcus aureus* (*S. aureus*) bacteria were completely killed by ZnO nanoparticles at concentrations $\geq 3.4$ mM and $\geq 1.0$ mM, respectively, with minimal effects on primary human T cells. More recent experiments have shown that these nanoparticles have superior ability to kill both Jurkat and Hut-78 cancer cells at micromolar concentrations at which normal cells displayed no measurable cell death. Such an order of magnitude difference in toxicity to cancer cells relative to normal host T-cells makes ZnO nanoparticles a potential candidate for cancer therapy. Based on these interesting results, we have developed a core-shell structure with fluorescent FITC encapsulated in $SiO_2$ as the core and nanoscale ZnO as a surface layer, hereafter referred as FITC-ZnO. These FITC-ZnO particles were synthesized using a novel one-pot methodology involving successive hydrolysis and condensation of FITC-linked silicate and zinc salt. The synergistic effects of ZnO and $SiO_2$ nanostructures on the optical properties of the fluorophores and the toxic nature of the resulting nanostructures are explored in detail. Moreover, although reactive oxygen species generated at the surface of excited nanomaterials are generally thought to be responsible for observed biocidal effects, the detailed mechanism of toxicity and their selective nature to different biological systems still remains poorly understood. Adding fluorescence functionality to the ZnO nanostructures will aid future detailed in vitro and in vivo studies necessary to understand the fundamental interaction/uptake mechanism as well as improve our ability to evaluate and efficiently utilize the therapeutic potential of ZnO nanoparticles. The present work focuses on the preparation and characterization of fluorescent FITC-ZnO particles with an untouched outer ZnO nanolayer and their ability to selectively kill certain types of cancer cells and bacteria. However, no attempt is made in this work to address the mechanism of cell-particle interactions and toxicity. These will be the subject matter of future publications.

Semiconducting ZnO has good chemical stability, wide direct band-gap ($Eg \approx 3.37$ eV) and large excitation binding energy (60 meV), and has been studied for numerous applications including nanodevices, light-emitting diodes, sensors, luminescence, and photovoltaics. Thus the ZnO surface layer of these novel core-shell FITC-ZnO nanostructures has the added benefit of providing a robust platform for many future applications. For example, Dorfman et al. (A. Dorfman, N. Kumar, J. Hahm, Langmuir, 22, 4890 (2006); and A. Dorfman, N. Kumar, J. Hahm, Adv. Materials, 18, 2685 (2006)) developed nanoscale ZnO platforms for use as attractive substrates in fluorescence bioassays using FITC labels. They found that ZnO nanorod substrates could significantly enhance the fluorescence detection capability of proteins and nucleic acids without any need for amplification of detection signal. Moreover, ZnO nanocrystals/quantum dots might produce UV and visible fluorescence. Thus, addition of a stable surface layer of ZnO on the fluorescent FITC-$SiO_2$ cores will provide the core-shell particles with two different fluorescence sources. Changes in the ZnO fluorescence when biological species are attached to the outer surface could provide opportunities for bio-sensing and the internal FITC fluorescence could serve as a reference standard to quantify relative change in intensity and the surface attached species. To the best of our knowledge, preparation and characterization of fluorescent dye encapsulated particles with an active ZnO finishing layer and their preferential cancer killing and bacterial inhibiting ability have not yet been reported.

SUMMARY OF THE INVENTION

Fluorescein isothiocyanate (FITC)-encapsulated $SiO_2$ core-shell particles with a nanoscale ZnO finishing layer have been synthesized for the first time as multifunctional "smart" nanostructures. Detailed characterization studies confirmed the formation of an outer ZnO layer on the $SiO_2$-FITC core. These ~200 nm sized particles showed promise toward cell imaging and cellular uptake studies using the bacterium *Escherichia coli* and Jurkat cancer cells, respectively. The FITC encapsulated ZnO particles demonstrated excellent selectivity in preferentially killing Jurkat cancer cells with minimal toxicity to normal primary immune cells (18% and 75% viability remaining, respectively, after exposure to 60 μg/mL) and inhibited the growth of both gram-positive and gram-negative bacteria at concentrations ≧250-500 μg/mL (for *Staphylococcus aureus* and *Escherichia coli*, respectively). These results indicate that the novel FITC encapsulated multifunctional particles with nanoscale ZnO surface layer can be used as smart nanostructures for particle tracking, cell imaging, antibacterial treatments and cancer therapy.

DETAILED DESCRIPTION OF THE PREFERRED EMBODIMENTS

Figure 1:
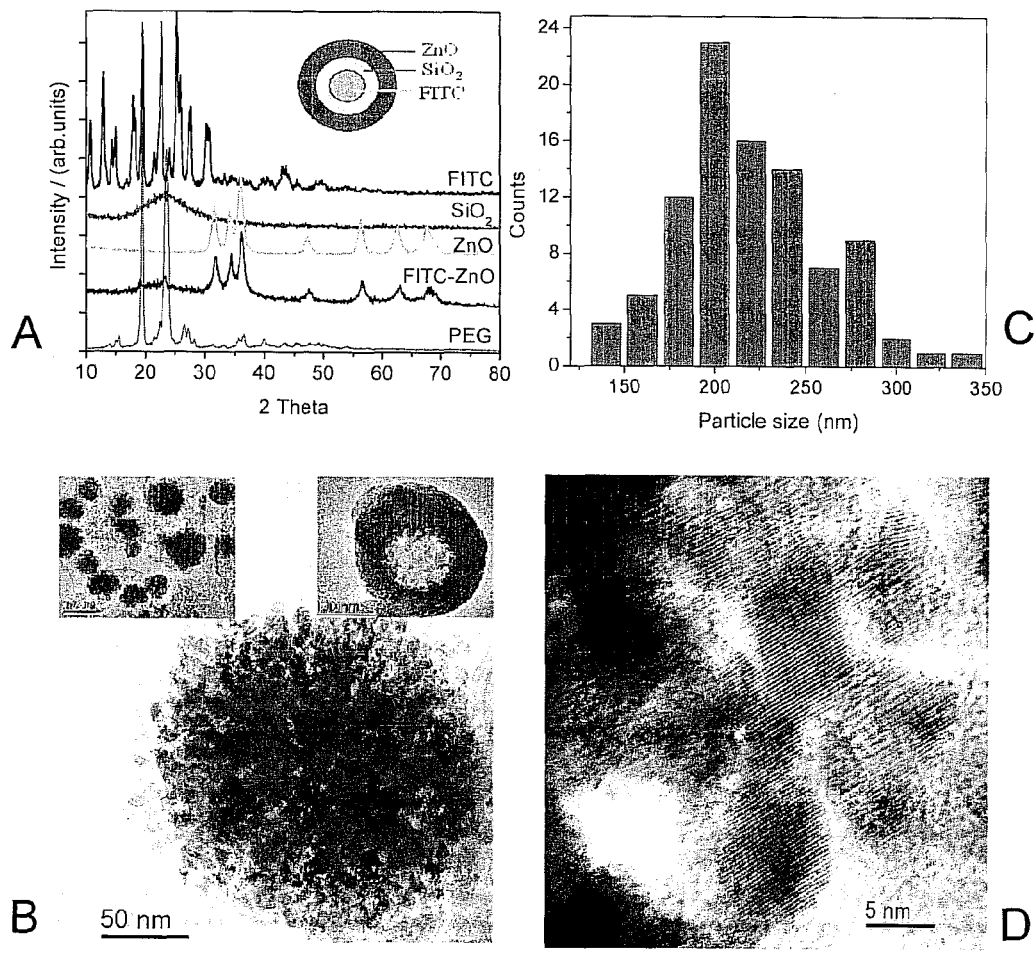
FIG. 1 is a collection of two charts and two transmission electron microscopy (TEM) images of FITC-ZnO particles.

Referring to the figures, there are shown some, but not the only, embodiments of the invented ZnO-encapsulated fluorescent dye particles, preferably FITC-ZnO particles. In the description that follows are some, but not the only, invented methods of making and using said ZnO-encapsulated fluorescent dye particles.

Experimental Section

Synthesis of FITC-ZnO Particles:

FITC-ZnO particles were synthesized by forced hydrolysis and condensation of FITC-binding silane and silicate to obtain the FITC-$SiO_2$ core, followed by the formation of ZnO surface layer using zinc salt. In a typical synthesis, 10 mg (0.026 mmol) of FITC was dissolved in 3.0 mL ethanol by stirring for 20 min, followed by the addition of 20 μL (0.085 mmol) of vacuum-distilled (3-aminopropyl)-trimethoxysilane (APTMS). The reaction continued for 24 h under stirring in the dark. The amino group of the APTMS reacts with the isothiocyanate group of FITC to form N-1-(3-triethoxysilylpropyl)-N'-fluoresceyl thiourea, and the resulting solution is referred to as FITC-APTMS. Second, 0.77 g tri-n-octylphosphine oxide (TOPO), 1.0 g polyethylene glycol (PEG), and 0.5 mL of FITC-APTMS were added to a flask containing 200 mL of diethylene glycol (DEG) solution and stirred for 10 min. Then, 0.5 mL of tetraethylorthosilicate (TEOS), 2.0 mL of water, and 1.5 mL of ammonium hydroxide (28-30%) were added into the above mixture and stirred for 1.5 h to form FITC-$SiO_2$ cores. A part of this sample was separated at this point to obtain FITC encapsulated silica particles to compare their properties with FITC encapsulated ZnO particles. The resulting mixture was then heated to 100° C. and 2.6 g of Zinc acetylacetonate, $Zn(CH_3COCHCOCH_3)_2$ was introduced. Following this, the mixture was heated to 160° C. and maintained at that temperature for 2 h. The heating was then stopped to allow the mixture to cool down to room temperature with continuous stirring for 1 h. The resulting FITC-ZnO particles were purified by centrifugation at 10,000 rpm for 8 min. The supernatant was removed and replaced with ethanol. This process was repeated for several times until no yellow fluorescence of FITC was observed in the supernatant. Subsequently, the resultant particles were dried in an oven.

Characterization of Fluorescent FITC-ZnO Particles:

The morphology, size, structure, and composition of FITC-ZnO particles were thoroughly investigated using transmission electron microscopy (TEM), X-ray diffraction (XRD), X-ray photoelectron spectroscopy (XPS), and UV-vis spectroscopy. (J. Hays, K. M. Reddy, N.Y. Graces, M. H. Engelhard, V. Shutthanadan, M. Luo, C. Xu, N.C. Giles, C. Wang, S. Thevuthasan, A. Punnoose, J. Phys: Condens. Matter. 19, 266203 (2007)). In addition to the as-prepared samples, XPS spectra were also collected after removing 2, 5, 8, and 11 nm thick layers successively via $Ar^+$ ion sputtering using a 2 kV $Ar^+$ ion beam rastered over a 4 mm diameter sample area during 2 RPM sample rotation.

The fluorescence properties and stability of FITC-ZnO particles were studied using fluorescence spectroscopy and flow cytometry. For flow cytometric analysis, a 3-color Epics XL cytometer (Coulter, Miami, Fla.) was used to evaluate the photobleaching and quenching effects of FITC-ZnO particle aggregates. FITC-ZnO particles were analyzed after keeping in oxygen-rich water for varying times, and in some cases, after subjecting the samples to illumination using a mercury lamp (Model SP200 spectrum tube, with 5000V and 10 mA output) and then resuspended in oxygen-rich water prior to analysis, and a minimum of 10,000 particle aggregates monitored for changes in relative fluorescence using a 488 nm argon laser.

Fluorescence spectra of FITC-ZnO particles were measured at room temperature using a Horiba Jobin Yvon T64000 spectrometer equipped with Hamamatsu R943-02 GaAs photomultiplier. Two lines of a He—Cd laser, 441.6 and 325 nm, were used for excitation. The photobleaching and quenching effects of the FITC-ZnO nanoparticles were investigated by measuring the fluorescence data at fixed time intervals after subjecting the samples to low power laser light (wavelength 441.6 nm, power density ~80 W $cm^{-2}$). Similar data were also taken from pure FITC sample under identical conditions for comparison.

Utility tests for cell imaging: The feasibility of using FITC-ZnO particles for particle tracking/cell imaging in biological environments was investigated using fluorescence confocal image microscopy (FCIM). Stationary phase *E. coli* cells were exposed to FITC-ZnO particles and PI for 15 minutes at room temperature. FITC-ZnO and PI exposed cells were spotted on a glass slide, allowed to air dry, and viewed using a Zeiss LSM 5 Pascal confocal microscope. Additional slides were prepared with *E. coli* cells exposed to either the FITC-ZnO particles or PI alone to determine if there was any overlap in the fluorescence emission of the two dyes. The confocal microscope was configured to prevent detection of FITC fluorescence in the PI channel and vice versa. For cellular uptake and internalization studies, log phase Jurkat cells were adhered to poly-d-lysine treated glass bottom chamber slides (MatTek, Ashland, Mass.), treated with 0.25 mM FITC-ZnO particles for 8 hours, washed three times in PBS/3% fetal bovine serum (FBS) to remove extracellular NP, stained with a PE-conjugated antibody specific to the CD3 cell surface protein (Beckman Coulter, Miami, Fla.) as previously described using 8 μl/200 μl of cells, and washed a final time in PBS/3% FBS. For confocal analysis, control slides were prepared to verify the absence of spectral overlap between the two dyes after appropriate instrument set-up.

Cancer/Anti-Bacteria Treatment Applications:

Toxicity of the FITC-ZnO particles toward human T lymphocytes and Jurkat cancer cells was determined as follows. First, peripheral blood mononuclear cells (PBMC) were obtained by Ficoll-Hypaque (Histopaque-1077, Sigma, St. Louis, Mo.) gradient centrifugation using heparinized blood samples from healthy volunteers. This cell mixture was washed 3 times with Hank's buffer (Sigma), and incubated at $1.0 \times 10^6$ cells/mL in RPMI-1640 (Sigma) containing 10% fetal bovine serum. $CD4^+$ T cells were subsequently isolated using negative immunomagnetic selection per manufacturer's instructions using a cocktail of antibodies against CD45RO, CD8, CD19, CD14, CD16, CD56, CD8, and glycophorin A (StemCell Technologies, Vancouver, B.C.) with collection of unlabeled T cells (typically >96% $CD4^+$ and >93% viable as assessed by flow cytometry). Purified $CD4^+$ T cells, or the Jurkat T cell line (ATCC, Rockville, Md.) were cultured in RPMI/10% FCS at $5 \times 10^5$ cells/mL in 96-well microtiter plates and treated with various concentrations of FITC-ZnO particles resuspended in PBS. For the delivery of FITC-ZnO particles to cell cultures, a stock solution was made and sonicated for 10 minutes. Then immediately prior to dispensing into each individual cell culture well, particles were vortexed and immediately dispensed. This process was repeated for each culture well, to reduce differential particle delivery due to sedimentation. After 24 h of culture, cells were stained with propidium iodide (PI; BD Biosciences, San Jose, Calif.) to monitor loss of membrane integrity as previously reported and 10 μL of fluorescently labeled microspheres (Molecular Probes, Eugene, Oreg.) added to each sample to allow for the absolute determination of cell numbers. Flow cytometry was used to analyze a minimum of 10,000 T cells per sample to determine changes in PI staining and quantification of cell death.

Similar toxicity studies of FITC-ZnO particles on bacteria were conducted. FITC-ZnO particles were resuspended in sterile 0.9% NaCl aqueous solution, then sonicated for 15 minutes in a bath sonicator and continuously agitated by pipetting prior to dispensing to LB media for toxicity testing. For inhibitory threshold determination resuspended FITC-ZnO particles were added to Luria-Bertani (LB) agar to different final concentrations (0-1250 □g/mL), as described in our earlier work. Time dependent toxicity tests were performed as follows. Equal densities of overnight *E. coli* cultures (based on $OD_{600nm}$ values) were used to inoculate LB broth with and without FITC-ZnO particles. Broth cultures were incubated with shaking as above, sampled repeatedly, and viable cell densities measured via CFU enumeration by plating on particle free LB media.

Results and Discussion

Synthesis, Structure and Composition of the Multi-Layered Core-Shell Architecture:

In this work, we have synthesized multifunctional fluorescent core-shell particles with a ZnO outer layer using a novel one-pot methodology of successive hydrolysis and condensation of FITC-incorporating silicate and zinc salt. This procedure is based on the methods used by several groups to synthesize colloidal silica particles encapsulated with organic fluorophores (A. Burns, H. Ow, U. Wiesner, Chem. Soc. Rev. 35, 1028 (2006); and H. Ow, D. R. Larson, M. Srivatsava, B. A. Baird, W. W. Webb, U. Wiesner, Nano Lett. 5, 113 (2005)), but modified to include the additional ZnO layer, as described in our earlier work. The novelty that this work brings to the field is the addition of the outer ZnO nanolayer to the FITC encapsulated silica that display an additional functionality of selective toxicity to certain types of bacteria and cancer cells. In the following, we demonstrate that the particles have a core-shell structure and they maintain the fluorescence properties of the encapsulated dye and the selective toxicity of the outer ZnO nanolayer.

The FITC encapsulated fluorescent ZnO particles were light orange in color. FIG. 1 (panels labeled A-D) shows X-ray diffraction patterns and HRTEM images of core-shell FITC-ZnO particles. FIG. 1A illustrates X-ray diffraction spectra of FITC-ZnO particles, along with those of pure samples of PEG, FITC, ZnO and $SiO_2$ particles, wherein a schematic illustration of the FITC-ZnO particles is shown in the inset of FIG. 1A. FIG. 1B shows TEM images of FITC-ZnO particles, where the inset on the left shows a group of FITC encapsulated ZnO particles and the right inset shows a TEM image of the FITC encapsulated $SiO_2$ particles taken out during the synthesis of FITC-ZnO particles. FIG. 1C is a plot showing the size distribution of FITC-ZnO particles, and FIG. 1D is a high-resolution TEM image of the outer shell of the FITC-ZnO particles illustrating the ZnO crystallites forming the outer layer.

The inset of FIG. 1A shows the schematic representation of the particle with the expected core-shell structure. X-ray diffraction (XRD) measurements were used to investigate the material composition and chemical phases present in the FITC-ZnO particles, comparing to those of pure samples of $SiO_2$ and ZnO particles prepared under similar conditions. The XRD spectrum of the FITC-ZnO particles shown in FIG. 1A clearly has all the expected ZnO peaks in addition to the strongest peaks of polyethylene glycol (PEG) used for size control and capping agent for $SiO_2$, and for improving the hydrophilicity of FITC-ZnO particles. Only a broad peak was observed for $SiO_2$ indicating poor crystallinity. Average size of the ZnO crystallites were estimated using the Scherrer equation, $L=0.9\lambda/\beta \cos \theta$ (where θ is the XRD peak position, λ is the x-ray wavelength and β is the width of the measured peak after correcting instrumental width). The estimated size of ~10 nm suggests that the outer ZnO layer was formed by attaching such nanocrystals on the surface of FITC encapsulated $SiO_2$ structures. Transmission electron microscopy (TEM) measurements were performed to investigate the particle size, shape and size distribution of the fluorescent FITC-ZnO particles.

FIG. 1B shows spherical FITC-ZnO particles of average size ~200 nm and with a size distribution shown in FIG. 1C. The TEM data also confirms the XRD result that the surface ZnO layer is formed via accumulation of ~10 nm sized ZnO crystallites (FIG. 1D). The presence of the relatively less electron transparent ZnO nanoparticle layer on the outer surface prevented clear observation of the core-shell structure. To obtain better insight on this, a part of the sample was separated during the synthesis process before adding the ZnO precursor. This provided FITC encapsulated silica particles before attaching the ZnO nanolayer on their surface. TEM of these FITC-SiO$_2$ particles showed an electron transparent core region (brighter region) presumably containing the FITC and the spherical silica shell (darker region) as shown in FIG. 1B (top right inset).

Figure 2:
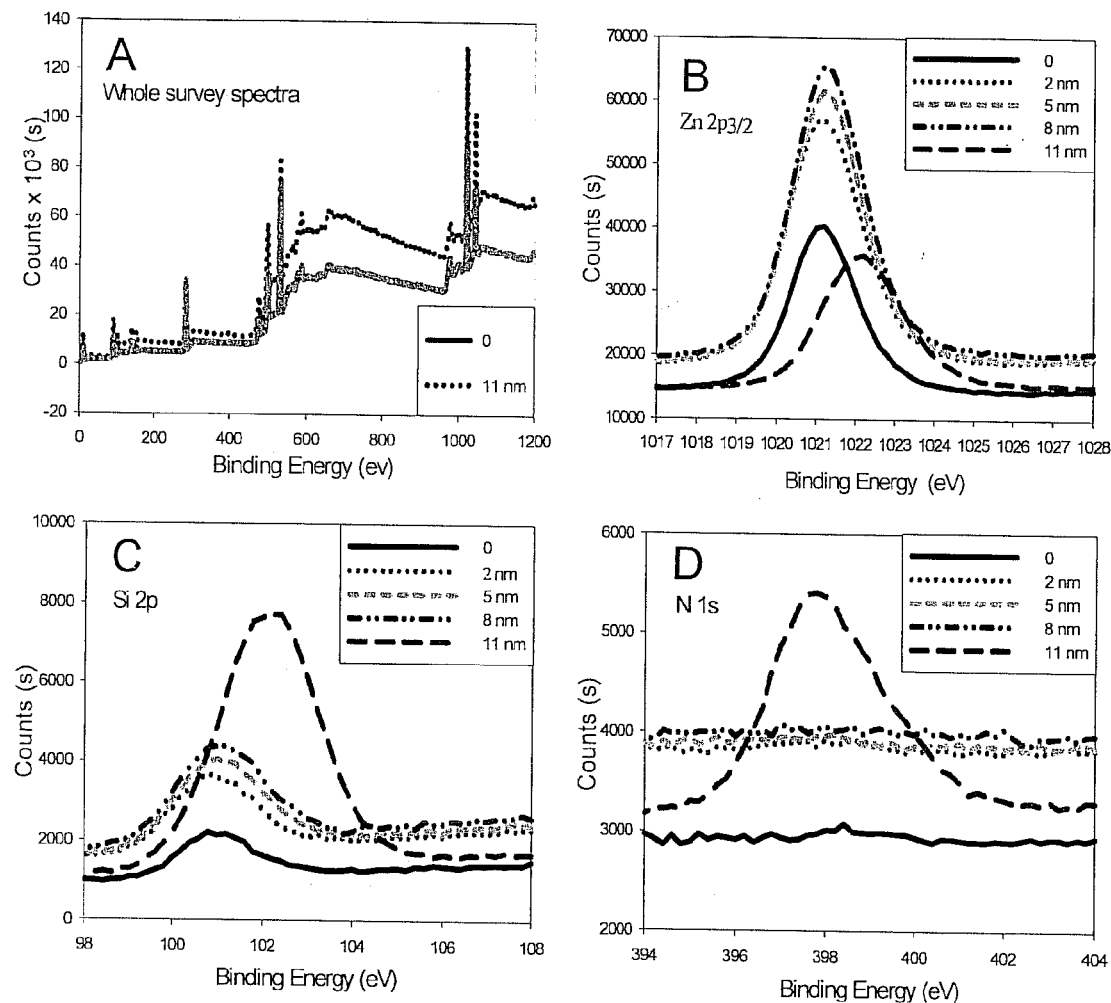
FIG. 2 is a collection of four charts about X-ray photoelectron spectroscopy (XPS) investigation of core-shell FITC-ZnO particles.

X-ray photoelectron spectroscopy (XPS) measurements were carried out to investigate the core-shell architecture of the fluorescent ZnO particles through layer-by-layer sputtering. FIG. 2 (panels labeled A-D) shows XPS investigation of core-shell FITC-ZnO particles, wherein FIG. 2A shows the XPS survey spectra of as-prepared FITC-ZnO particles and the same after removing 11 nm using Ar ion sputtering, a "whole survey spectrum." FIGS. 2B, C and D show the high-resolution XPS spectra of the Zn 2p$_{3/2}$, Si 2p, and N 1s regions, respectively, collected from as-prepared samples as well as from samples after successively removing 2, 5, 8 and 11 nm thick layers. Thus, FIGS. 2B-D show the high resolution core level spectra of the Zn 2p$_{3/2}$ (FIG. 2B), Si 2p (FIG. 2C) and N 1s (FIG. 2D) regions, which are representative and distinct constituents of the ZnO, SiO$_2$ and FITC layers. FIG. 2B shows the Zn 2p$_{3/2}$ peak at 1021.4 eV which is the expected binding energy range for pure ZnO. The observed increase in the peak intensity on going from the surface of the as-prepared particles to 8 nm deep indicated more efficient packing of ZnO crystallites with increasing depth. However, further sputter removal up to 11 nm showed a drastic reduction in the peak intensity and ~1.0 eV increase in the binding energy. This is indicative of a significant change in the chemical environment, most likely a transition from the ZnO surface layer to a SiO$_2$ inner layer. Based on the observed presence of Zn in particles that underwent an 11 nm sputter removal and considering the $\leq$12 nm analysis depth, an approximate thickness of 11-23 nm may be estimated for the ZnO surface layer. This estimate matches with the conclusion from the TEM and XRD data that the surface ZnO layer was formed by attaching ~10 nm sized ZnO crystallites on the SiO$_2$ surface. These results are further confirmed by the Si 2p peaks shown in FIG. 2C. Weaker Si 2p peaks are present even in the as-prepared samples. The nominal analysis depth of XPS is in the $\leq$12 nm range and therefore, if the SiO$_2$ layer starts about 8-12 nm below the particle surface, a weak Si 2p signal from the outer walls of the SiO$_2$ layer is expected in the as-prepared sample as well as in samples after removing few nm thick layers. However, similar to the case of Zn 2p$_{3/2}$ data shown in FIG. 2B, the Si 2p peak also shows dramatic changes when a 11 nm thick layer is removed from the sample (FIG. 2C). The Si 2p signal intensity increases significantly and shifts to higher energies by 1.4 eV. This large shift indicating a significant increase in the Si 2p binding energy can be attributed to the covalent bonding of Si ions on the inner walls of the SiO$_2$ layer with FITC molecules.

Recalling that FITC is bound covalently to the silica matrix via the (3-aminopropyl)-trimethoxysilane (APTMS) coupling agent, the results shown in FIGS. 2B and 2C indicate a layered structure of the order of ZnO—SiO$_2$-APTMS-FITC as we proceed from the surface to the core of the FITC-ZnO particle. At the boundaries of these different layers, some level of mixed interface is also expected. The N 1s peak arising from the FITC molecules shown in FIG. 2d further support the presence of such a layered architecture for the FITC-ZnO particles. Unlike the Si 2p peak, no N 1s peak (397.8 eV) was observed in the as-prepared samples suggesting that a measurable concentration of FITC molecules are not present in the surface region of the particles, at least in the $\leq$12 nm analysis depth range of XPS. The complete absence of this peak in as-prepared samples as well as in the ones after the sputter removal of up to 8 nm, and its subsequent strong presence after removing 11 nm confirm that FITC is mostly concentrated in the core of the particles. However, since the amino group of the APTMS reacts with the isothiocyanate group of FITC and this coupled FITC-APTMS participates with tetraethylorthosilicate (TEOS) in the hydrolysis/condensation reactions, some distribution of FITC molecules in the silica shell, especially in the inner layer is a likely possibility.

The binding energy shifts of the Zn 2p$_{3/2}$ peak and the Si 2p peak in the 11 nm sputter removed sample are not due to any random changes or charging effects because (i) the sample charging has been continuously compensated during the sputtering process by comparing the effect on known standards, (ii) if the binding energy shifts are due to any charging effect, it should display a gradual and systematic shift as sputtering (or charging) progresses, (iii) the peak shifts at 11 nm sputtering is associated with large changes in the intensities also indicating that the effect is related to transition between layers and the associated changes in the concentration of the elemental constituents, and (iv) the change in the XPS peaks at 11 nm sputtering coincides with the appearance of the N 1s signal from the FITC layer, again suggesting that the observed binding energy changes are associated with changes in the chemical environment/binding as data is collected progressively from different layers.

Figure 3:
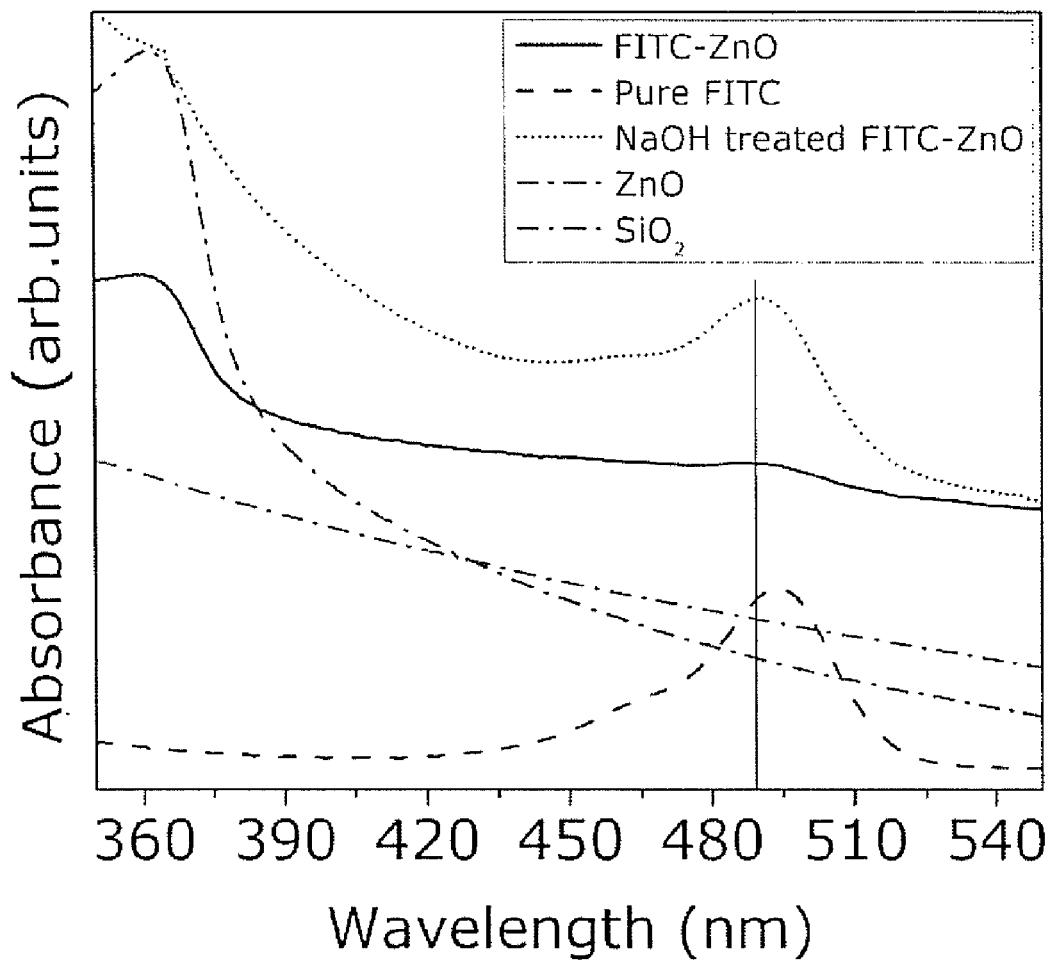
FIG. 3 is a chart about UV-vis-NIR absorption spectra of FITC-ZnO particles.

The optical properties of FITC-ZnO particles in water were studied using UV-vis-NIR spectrophotometry in the absorption mode. The spectrum of the FITC encapsulated ZnO samples was the sum of the spectral features observed in pure samples of ~10 nm ZnO particles, ~150 nm SiO$_2$ and pure FITC measured separately, as illustrated in the absorption spectra in FIG. 3. FIG. 3 discloses UV-vis-NIR absorption spectra of FITC-ZnO particles. The optical spectra of FITC-ZnO particles dispersed in water (40 mg/mL) along with pure samples of FITC ($1.2 \times 10^{-6}$ M), ZnO and SiO$_2$, and of the FITC-ZnO particles after treatment of 1.5% NaOH to release the encapsulated FITC by dissolving the ZnO—SiO$_2$ shells (NaOH treated FITC-ZnO).

The features near 362 nm in pure ZnO and FITC-ZnO are the well expected absorption edges corresponding to the band gap of ZnO. The absorption peak at 489 nm of the encapsulated FITC molecules was lower than 494 nm observed for pure FITC. This small blue shift could be the result of covalent binding of the FITC molecules on the silica shell as also evident from the XPS data discussed earlier, and/or the presence of electron rich ZnO surface layer that might electromagnetically interact with the fluorophore. The charges in ZnO and/or near the polar ZnO—SiO$_2$ interface might give rise to long-range electrostatic potential, which might extend through the silica layer to the FITC core. Another possible reason might be a direct binding of a fraction of the FITC molecules distributed in the silica shell (through the pores present in the silica layer) with ZnO nanocrystals. Additionally, UV-vis-NIR measurements were conducted for the FITC-ZnO particles after treating with 1.5% NaOH to release the encapsulated dye. The NaOH addition dissolves the ZnO layer as evident from the disappearance of the band edge (FIG. 3). From this experiment, it was found that 40 mg/mL of the FITC-ZnO particles dispersed in water might have encapsulated FITC equivalent to $1.2 \times 10^{-6}$ M of FITC, estimated by comparing the UV absorbance with that of pure dye solution.

Figure 4:
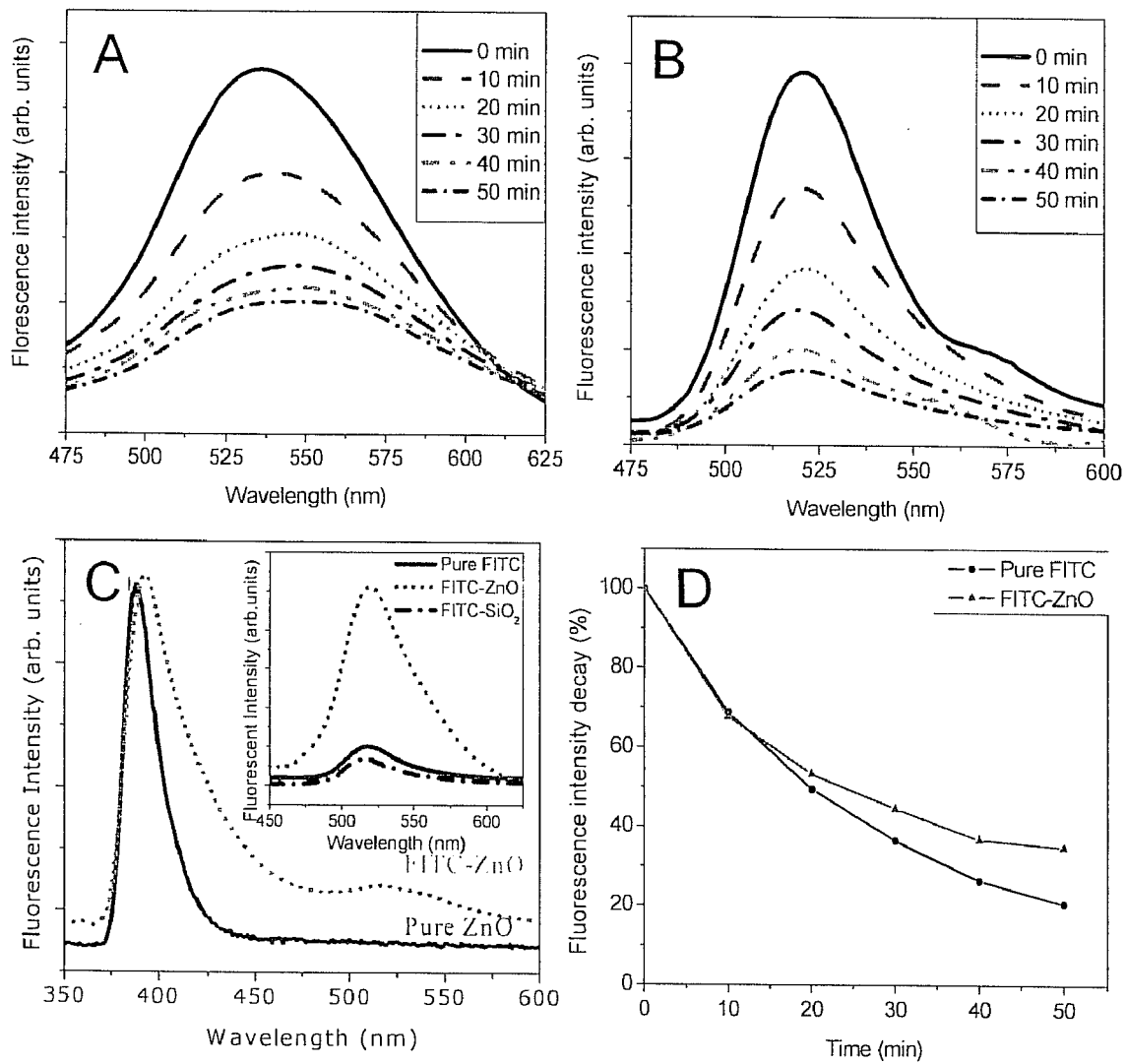
FIG. 4 is a collection of four charts about fluorescence characterization of FITC-ZnO particles.

Fluorescent Emission Characteristics:

The FITC-ZnO particles are capable of emitting strong fluorescence both in the visible and UV wavelength ranges originating from FITC and ZnO layers, respectively. FIG. 4

(panels labeled A-D) shows fluorescence characterization of FITC-ZnO particles, wherein FIG. 4A shows fluorescence emission spectra of FITC-ZnO particles and FIG. 4B shows fluorescence emission spectra of pure FITC ($1.2 \times 10^{-6}$ M), both of which were dispersed in oxygen-rich water and measured as a function of time shown. FIG. 4C shows the comparison of UV fluorescence spectra between FITC-ZnO particles and pure ZnO nanoparticles. The inset in FIG. 4C shows the FITC fluorescence from pure FITC, FITC encapsulated $SiO_2$ and FITC encapsulated ZnO; and the plot in FIG. 4D shows the relative decrease of fluorescence intensity as a function of exposure time for pure FITC sample and FITC encapsulated ZnO particles.

Specifically, FIGS. 4A and 4B show the visible region fluorescence emission of FITC-ZnO particles and pure FITC (dispersed in water), respectively, excited by the 441.6 nm laser light. The encapsulation of FITC in the $SiO_2$ and ZnO layered shell might have caused a slight red shift and broadening, as shown in the insert of FIG. 4C. Interestingly, dye encapsulated $SiO_2$ displayed a blue shift due to the covalent binding of the dye molecules as observed by other groups also. The change of the FITC fluorescence emission when the additional ZnO layer was added is attributed to the electromagnetic interactions between the ZnO layer and the FITC molecules and/or a direct binding of some FITC molecules distributed in the silica shell as discussed earlier. Colloidal metal layers on silica nanoparticles have been reported to exhibit plasmon resonance and can significantly modify the fluorescence emission properties of the encapsulated dye molecules. The polar semiconducting ZnO surface layer might also have caused an electromagnetic interaction with FITC to exhibit the observed changes. Similar experiments employing a 325 nm UV laser produced strong UV fluorescence from ZnO layer shown in FIG. 4C. The peak emission from ZnO in FITC-ZnO particles is similar to that of ~10 nm-sized pure ZnO particles, but occurs at slightly longer wavelength (392 nm) compared to the emission from pure ZnO (387 n). This shift is most likely due to the presence of the $SiO_2$ layer and/or the binding of FITC molecules present in the silica layer in close proximity. The UV laser and the resulting UV fluorescence from the ZnO layer also excite green fluorescence from the FITC dye, as can be seen in inset of FIG. 4C. Several groups have recently began developing ratiometric pH sensors which rely on the changes in the intensity, wavelength as well as other fluorescence characteristics of a dye attached to the surface of a core-shell nanoparticle due to analyte interactions. The inner dye encapsulated in the silica particles acts as an internal standard for the ratiometric analysis. Our demonstrated ability to integrate an additional layer of UV fluorescent ZnO thus provides the core-shell particles two fluorescence sources. By choosing appropriate dye molecules and layered architectures, ZnO based core-shell particles could also form efficient platforms for ratiometric sensing applications.

The utility of fluorescent particles for tracking and imaging applications depends also on the environmental and photo-stability of the fluorescence emission. The fluorescence emission of a fluorophore is often affected by the molecular interaction between the dye and various active species in the solvent such as dissolved oxygen. To investigate the environmental and photo-stability, the FITC-ZnO particles were dispersed in oxygen-rich water and its fluorescence emission was recorded using a fluorescence spectrometer as a function of the time of laser exposure, shown in FIG. 4A. The observed changes are compared to a similar measurement conducted on micromolar concentrations of pure FITC dissolved in water, shown in FIG. 4B. A plot of integrated fluorescence intensity versus the laser light exposure time (441.6 nm line), shown in FIG. 4D, suggests that the $SiO_2$—ZnO layer offers protection against photobleaching of the FITC molecules. The decay time constants $t_0$ for pure FITC and the FITC-ZnO particles estimated from fitting the data shown in FIG. 4d with exponential decay function $e^{-t/t_0}$ were 17 and 27 minutes respectively. Evidently, the photo-stability of FITC-$SiO_2$ particles reported by other groups is much more significant than our results. We believe that the reasons for this relatively weaker photo-stability might be the high concentration of FITC in the core of the particles and the less uniform distribution of FITC in $SiO_2$. Future efforts will focus on improving the photo-stability.

Figure 5:
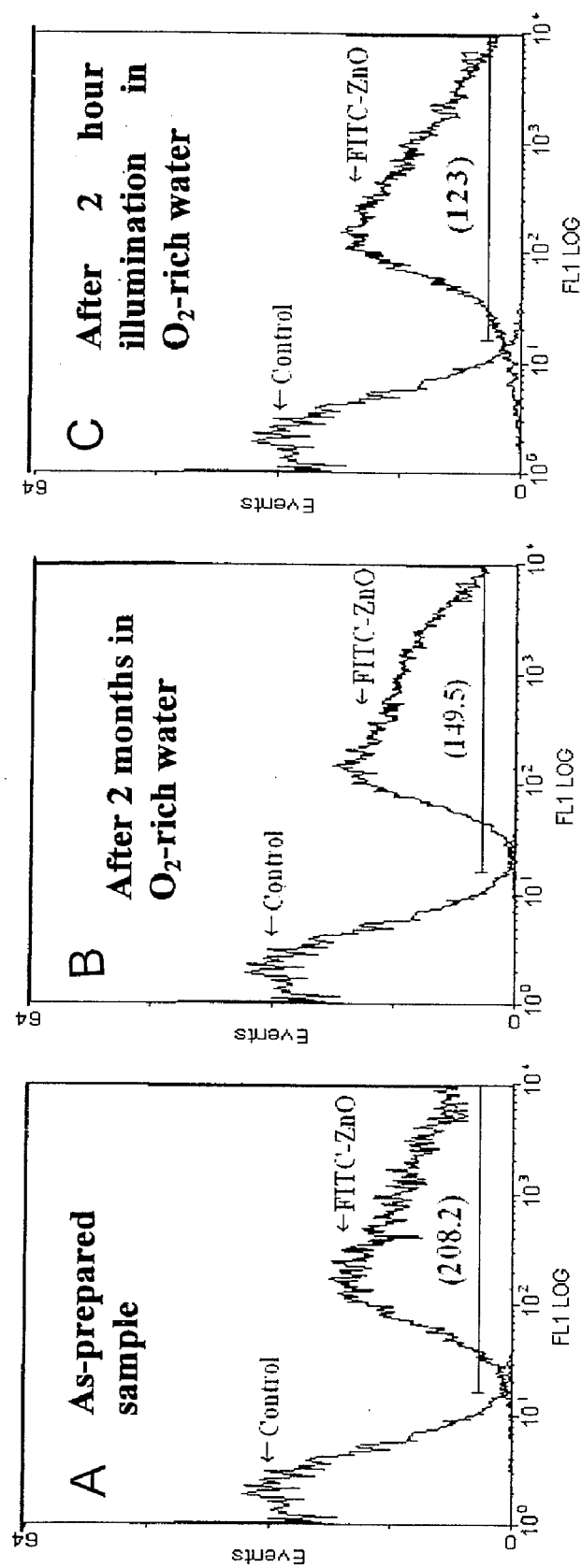
FIG. 5 is a collection of three charts about flow cytometry examination of FITC-ZnO particles.

Flow cytometry is a commonly used biological/biomedical research tool and the ability of the fluorescent FITC-ZnO particles for use with this technique was carefully investigated (FIG. 5). FIG. 5 (panels labeled A-D) shows flow cytometry examination of FITC-ZnO particles. The data for FITC-ZnO particles taken (FIG. 5A) immediately after dispersing in oxygen-free water, (FIG. 5B) after keeping in oxygen-rich water for 2 months and (FIG. 5C) after exposure to a mercury lamp for 2 h. Nanoparticle aggregates were gated based on their forward scatter and side scattering light properties on a log scale with collection of 10,000 events. This identical gating region was subsequently used to determine the relative mean FL1 fluorescence signal of FITC-ZnO particles after various treatments. Unlabeled ZnO particles were used as the control sample in these experiments and numbers inside parenthesis indicate mean fluorescence intensity (MFI) of FITC-ZnO particles.

A high percentage (98%) of the freshly synthesized FITC-ZnO particle aggregates dispersed in oxygen-free water was derivatively fluorescent. As shown in FIG. 5a, a strong fluorescent signal (mean fluorescence intensity, MFI=208.2) was observed in freshly prepared FITC encapsulated particle aggregates compared to the unlabeled pure ZnO particles. Long tem protection against photobleaching was also investigated using flow cytometry (FIG. 5, panels labeled A-C). For these experiments, FITC-ZnO particles were either kept in oxygen-rich water for a significantly longer period of two months (FIG. 5B) or illuminated for 2 h with a mercury lamp and then dispersed in oxygen-rich water media (FIG. 5C). Based on comparisons of the fluorescence intensities to freshly prepared FITC-ZnO particle aggregates (FIG. 5A, MFI 208.2), the fluorescence signal remained considerably stable (between 59-72%) either after storage for two months (FIG. 5B, MFI 149.5) or exposure to strong light (FIG. 5C, MFI 123) suggesting the vital role of the $SiO_2$—ZnO shell in protecting the dye from bleaching.

Figure 6:
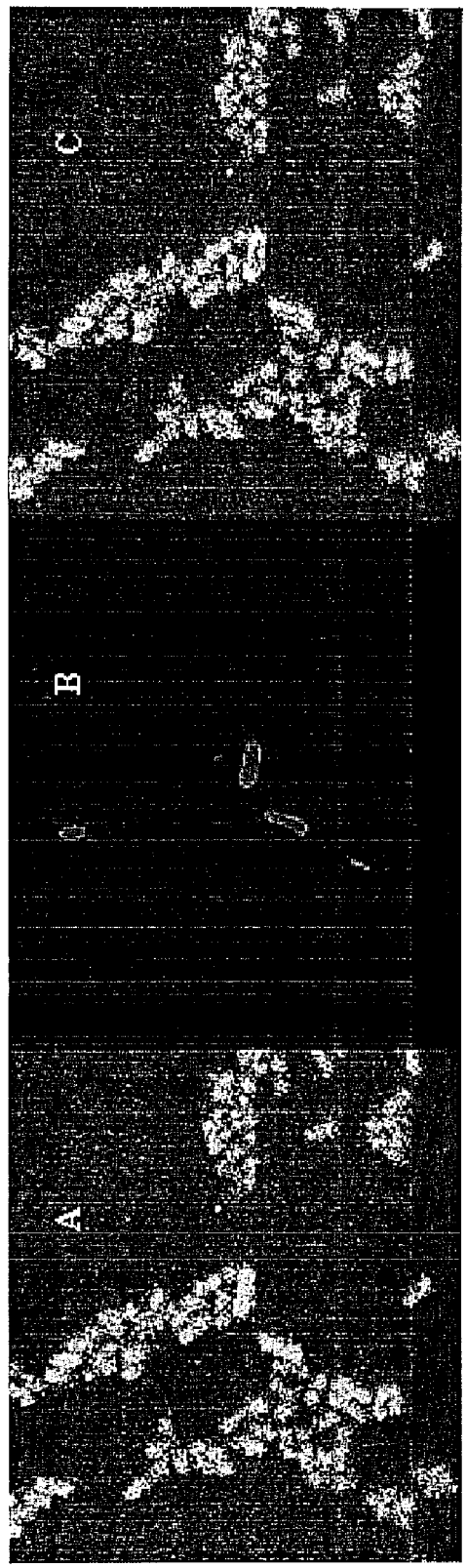
FIG. 6 is three microscopic cell images with FITC-ZnO particles.

Biomedical Applications, Cell Imaging, Particle Uptake and Selective Toxicity:

We demonstrate the ability of FITC-ZnO particles for potential use in four novel biomedical applications—(i) cell imaging, (ii) eukaryotic cellular uptake of particles, (iii) anti-bacterial treatment and (iv) cancer treatment. Dye encapsulated silica particles have been used in the past for biological imaging by attaching cell specific antibodies on the outer silica surface. For example, Ow et al. have successfully labeled rat basophilic leukemia mast cells using antibody (immunoglobulin E) adsorbed fluorescent silica particles and the FceRI receptor available on these cells. It is often desirable to observe markers for extended periods of time against the background of intrinsic cellular emissions. Accordingly, we have investigated the ability of FITC-ZnO particles (at 7.5 μg/mL) dispersed in saline medium to image *E. coli* using the green fluorescence of the particles (FIG. 6). *E. coli* cells were simultaneously stained with FITC-doped ZnO particles (green fluorescence), and the vital dye (propidium iodide (PI), red fluorescence). PI uptake by bacterial cells is dependent on loss of cell membrane integrity and is, therefore, frequently used to indicate the extent of death in a cell population. Bacteria co-treated with FITC-ZnO and PI were examined by confocal microscopy to establish the ability of the FITC-ZnO particles to stain/visualize bacterial cells (FIG. 6). FIG. 6 (panels labeled A-C) shows cell imaging with FITC-ZnO particles. Confocal fluorescence microscopic images of *E. coli* cells simultaneously treated with FITC-doped ZnO particles (green fluorescence) and propidium iodide (PI, red fluorescence), showing (FIG. 6A) fluorescence signal from FITC-ZnO, (FIG. 6B) fluorescence signal from PI, and (FIG. 6C) overlay of FITC-doped ZnO and PI signals, yellow cells indicate dual stained cells.

Such a bivariate analysis allows for the discrimination of intact cells (FITC only) and dead/non-viable cells (FITC and PI). Visualization of the FITC-ZnO signal alone indicates that the FITC-ZnO particles were associated with the bacterial cells and emitting very bright green fluorescence (FIG. 6A). Visualization of PI signal alone indicated presence of *E. coli* cells with damaged and permeable cell membranes (FIG. 6B). By overlaying the FITC-ZnO and PI signals, a third image was generated where *E. coli* cells stained with both FITC-ZnO and PI appear yellow (FIG. 6C). The confocal images clearly demonstrate that FITC-ZnO particles have an excellent ability to image cells using common imaging techniques if they can be attached to cells of interest. This image indicates that many of the FITC-ZnO associated *E. coli* cells are still viable (i.e. not many yellow cells in panel C) even though the FITC-ZnO particles can be toxic to *E. coli* cells. This is likely due to the short incubation time (15 minutes) used to prepare the cells for imaging. The granular appearance of the *E. coli* cells (FIG. 6A) is due to the particulate nature of the FITC-ZnO. As discussed above the FITC-ZnO particles are ~200 nm in diameter and close to the resolution of the confocal microscope. The granular appearance of the *E. coli* cells is likely due to adherence of the particles to the external surface of the cells and the ability of the microscope to resolve individual fluorescent particles or groups of particles. It may be noted that the purpose of this experiment is only to demonstrate the potential of FITC-ZnO particles as a fluorescence probe and not to demonstrate selectivity in the cell-nanoparticle (FITC-ZnO) interaction. For many cell types, binding of cell specific antibodies might be necessary for selective cell imaging applications.

Figure 7:
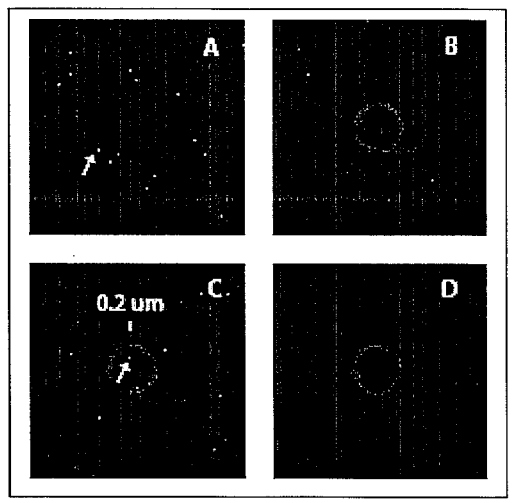
FIG. 7 is four microscopic images about uptake of FITC-ZnO particles by Jurkat cancer cells.

Given that the size of the FITC-doped particles (~200 nm) described in this study and the diameter of the imaged bacterial cells (~500 nm) are near the resolution capabilities of the microscope, nanoparticle uptake and internalization studies were performed on eukaryotic Jurkat T cells as an example system. The cells were treated with FITC-ZnO particles (green fluorescence) for 8 h, and then washed extensively to remove unattached extracellular particles and reduce background staining. Cells were then stained with a PE-conjugated antibody directed against the CD3 membrane-bound protein (red fluorescence) and confocal images taken using live cells to avoid internalization artifacts resulting from cell fixation. FIG. 7 (panels labeled A-D) shows uptake of FITC-ZnO particles by Jurkat cancer cells. Confocal fluorescence microscopic images of Jurkat cancer cells treated with 0.25 mM FITC-ZnO particle (green fluorescence) for 8 hours and stained with a PE-conjugated antibody specific to CD3 cell surface protein (red fluorescence) with extensive washing to remove extracellular NP. FIG. 7A depicts FITC-ZnO particles alone (after identical washing steps as samples containing cells) with an arrow indicating a typical particle of ~200 nm. FIGS. 7B-D show consecutive cell images/slices of a single cell. In FIG. 7C, an internalized particle of expected 200 nm size is indicated by an arrow and orthogonal viewing was used to confirm particle intracellular localization.

FIG. 7 shows consecutive three-dimensional slices through a single Jurkat T cell (panels B-D) demonstrating the internalization of a green fluorescent FITC-ZnO particle with intracellular localization being confirmed by viewing along orthogonal directions (not shown). Individual confocal image slices were taken at intervals of 200 nm thickness (comparable in size to the NP), thus only one internalized particle is shown in the presented focal plane. However, at least six internalized NP were observed in this particular cell with additional internalizations likely but too proximate to the plasma membrane to accurately resolve. The presence of such internalized FITC-ZnO particles was confirmed in multiple cells present on the culture slide. The image in panel A reflects NP background staining and was obtained by treating a chamberslide with an identical concentration of NP and sample washing regime as for cell cultures. It is important to note that the goal of this particular study was to specifically show NP uptake and intracellular localization in intact T cells following a short NP exposure prior to extensive cytotoxicity being manifested in contrast to simply observing NP association with cells (either extracellular or intracellular) as performed for FIG. 6. Although no attempt has been made in this work to ascertain the specific intracellular locations of the internalized particles, this important topic will be the subject matter of future studies.

Figure 8:
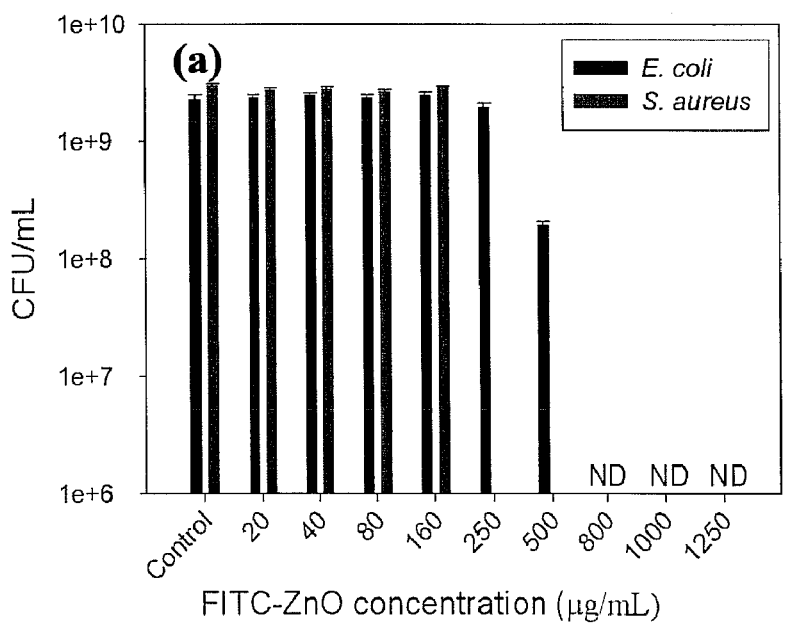
FIG. 8 is a collection of two charts about concentration and time-dependent cytotoxicity of FITC-ZnO particles for bacterial systems.
Figure 8B:
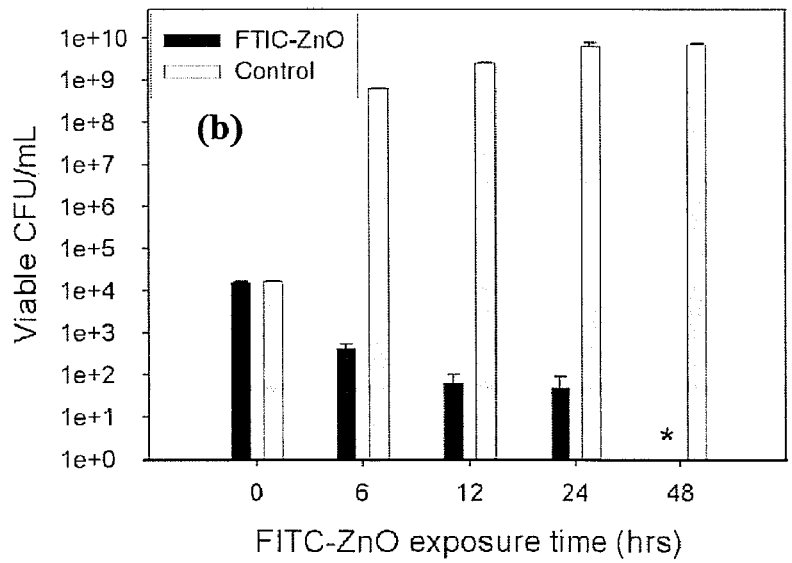

We have recently shown that ZnO nanoparticles can selectively kill certain bacteria including *E. coli* and *S. aureus*. Here we demonstrate a similar ability of FITC-ZnO particles to inhibit the growth of these two organisms. FIG. 8A shows the number of bacterial colony forming units (CFU) produced by *E. coli* and *S. aureus*, after being grown in the presence of FITC-ZnO particles overnight. FITC-ZnO particles prevented growth of *E. coli* at concentrations $\geqq 500$ μg/mL, whereas concentrations $\geqq 250$ μg/mL prevented growth of *S. aureus*. The relative difference in toxicity of FITC-ZnO particles to *E. coli* and *S. aureus* is similar to that previously reported by our group for ZnO nanoparticles,[11] thus suggesting that the FITC-ZnO particles retain bacterial toxicity similar to the pure ZnO nanoparticles. Additional, time dependent exposures were conducted by enumerating CFU of *E. coli* after 0, 6, 12, 24 and 48 hours of FITC-ZnO particle exposure (FIG. 8B). Exposure to FITC-ZnO particles resulted in cell death at concentrations of 800 μg/mL with number of viable bacterial cells reduced to below 99.9% of the initial CFU/mL within 12 hours. Viable cells were completely absent after 48 hours of treatment.

We have also recently determined that ZnO nanoparticles show no significant toxicity to primary human T cells. To determine whether FITC encapsulated particles with nanoscale ZnO outer surface can retain the ability of differentially killing cancer cells, new experiments were conducted. Flow cytometry was used to determine the number of viable human cancerous T cells compared to normal primary T cells after exposure to FITC-ZnO particles for 24 h. FIG. 8 shows concentration and time dependent cytotoxicity of FITC-ZnO particles for bacterial systems. In FIG. 8A, *E. coli* and *S. aureus* cells were plated on LB media containing varying concentrations of FITC-ZnO particles and incubated at 37° C. for 24 h. Bars represent means±standard errors (n=3), ND indicates concentrations at which no bacterial colonies were detected after 48 h of incubation. In FIG. 8B, there is shown effect of ZnO NP exposure time on the viability and growth of *E. coli*. (Plot presents mean CFU/mL (±standard error, n=3) of *E.*

Coli exposed to 800 μg/L FITC-ZnO particles for 0, 6, 12, 24, and 48 hours, and * in the figure indicates measured ZnO concentrations at which no CFU counts of *E. coli* were observed.)

Figure 9:
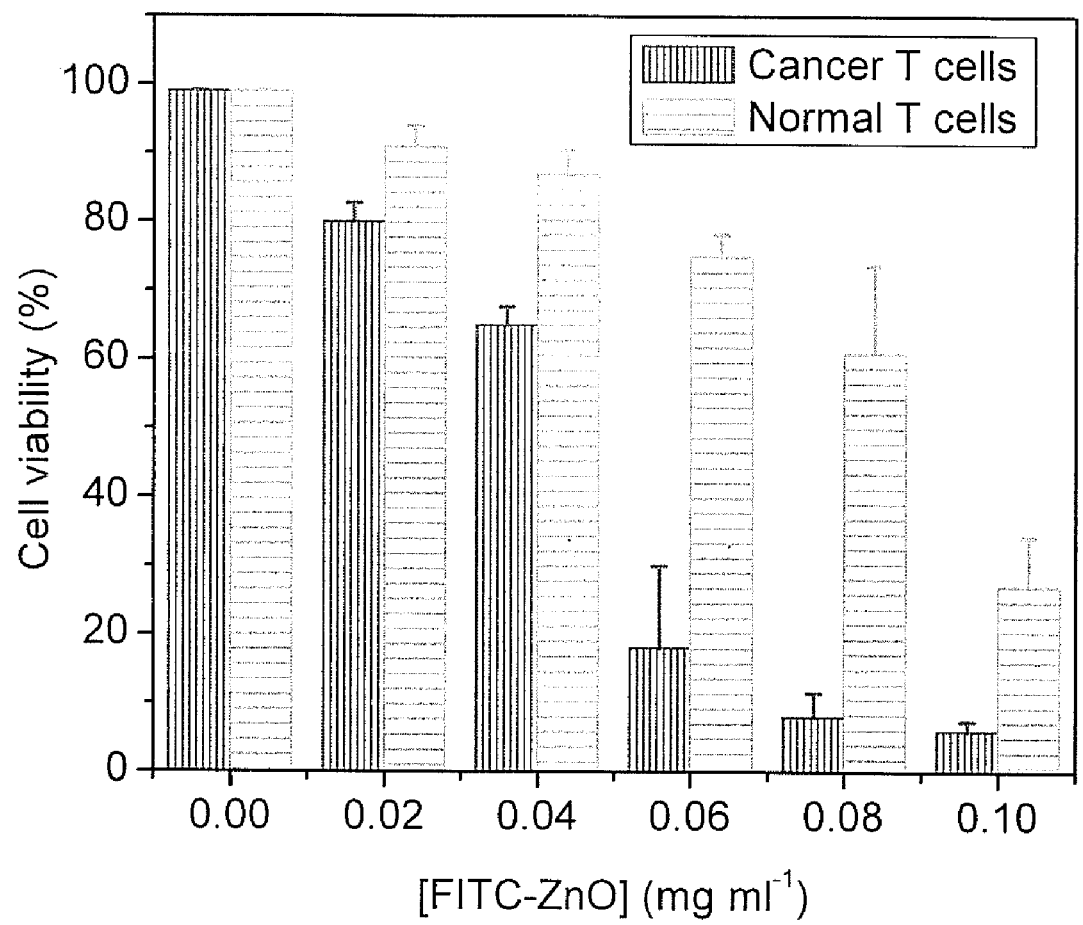
FIG. 9 is a chart about concentration-dependent cytotoxicity of FITC-ZnO particles for leukemia T cells and normal human T cells.

FIG. 9 shows that FITC-ZnO particles reduced cell viability of Jurkat T leukemia cells to 8% at concentrations ≧80 μg/mL, whereas the viability of normal CD4$^+$ T cells at this concentration remained at ~61%. Importantly, the differential toxicity of FITC-ZnO particles to cancerous and normal body cells is similar to observations in our lab involving unlabeled ZnO nanoparticles and indicates a potential new utility of ZnO nanoparticles in the treatment of human cancers.

The novel biomedical applications—cell imaging, antibacterial treatment and cancer treatment—of the FITC-ZnO particles were conducted primarily to demonstrate their multifunctional nature. The performance of these particles in the above demonstrated applications could be further enhanced by improving the quality and properties of these particles such as the particle size, uniformity, concentration of FITC molecules per particles among others and these aspects will be addressed in future studies.

CONCLUSIONS

We have successfully developed fluorescent particles with a nanoscale ZnO finishing layer using a novel one-pot synthesis methodology. Although dye encapsulated fluorescent core-shell SiO$_2$ particles have been successfully synthesized in the past with or without a metal layer on the outer surface, this is the first time a semiconducting oxide layer, nanoscale ZnO, has been attached to the particles. A variety of characterization studies, most notably systematic XPS measurements after sputter removing nanometer thick layers, confirmed the presence of the multi-layered architecture in the order ZnO—SiO$_2$-FITC as we proceed from the surface to the core of the ~200 nm sized particles. Such direct experimental confirmation of the multi-layered structure in core-shell particles has not been demonstrated in the past. Optical studies confirmed the ability of the ZnO based core-shell particles to improve the environmental and photostability of the fluorescent dye. This makes these particles very useful for imaging cells using their relatively stable fluorescent emission.

The additional ZnO layer in our core-shell particles opens up a variety of applications using the attractive physical and chemical properties of nanoscale ZnO including the following novel features demonstrated in this work:

1. Fluorescence probe for biological applications such as cell imaging and particle tracking.
2. Selective toxicity to bacteria suggesting their potential for antibacterial applications.
3. Ability to preferentially kill cancer cells without comparable effects on normal human immune cells, suggesting its potential for nanomedicinal applications.

In addition the nanoscale ZnO layer might also offer new opportunities in the fluorescence detection of biomolecules by acting as a high surface area sensor platform. The UV fluorescence of the incorporated ZnO layer and the internal FITC fluorescence might provide new opportunities to detect and quantify surface attached biological and chemical species. Thus the multifunctional ZnO based fluorescent particles offers wide ranging opportunities in the nano-bio-technology applications.

Although this invention has been described above with reference to particular means, materials, and embodiments, it is to be understood that the invention is not limited to these disclosed particulars, but extends instead to all equivalents within the scope of the following claims.

The invention claimed is:

1. A composition of matter comprising a fluorescent dye core nanostructure with a nanoscale ZnO surface layer.

2. The composition of claim 1 wherein the combination of the core nanostructure and nanoscale surface layer are about 200 nm.

3. The composition of claim 1 wherein the ZnO surface layer is about 10 nm.

4. A method of making a fluorescent dye core nanostructure with a nanoscale ZnO surface layer, the method comprising successive hydrolysis and condensation of organic dye molecules incorporating silicate and a zinc salt.

5. The method of claim 4 wherein the organic dye molecules comprise fluorescein isothiocyanate.

6. A method of making a fluorescent dye core nanostructure with a nanoscale Zn surface layer comprising:
   first forming organic dye molecules encapsulated by SiO$_2$ by micro-emulsion; and
   then coating the SiO$_2$-encapsulated organic dye molecules with a ZnO layer by hydrolysis of a zinc salt.

7. The method of claim 6 wherein the organic dye molecules comprise fluorescein isothiocyanate.

8. A method of killing cancer cells using a fluorescent dye core nanostructure with a nanoscale ZnO surface layer while monitoring the nanostructure with a fluorescence detector.

9. A method of killing bacteria cells using a fluorescent dye core nanostructure with a nanoscale ZnO surface layer while monitoring the nanostructure with a fluorescence detector.

* * * * *